United States Patent [19]

Ooishi

[11] Patent Number: 4,684,634

[45] Date of Patent: Aug. 4, 1987

[54] AGRICULTURAL AND HORTICULTURAL FUNGICIDAL COMPOSITION

[75] Inventor: Tadashi Ooishi, Toyonaka, Japan

[73] Assignee: Sumitomo Chemical Company, Limited, Osaka, Japan

[21] Appl. No.: 809,856

[22] Filed: Dec. 18, 1985

Related U.S. Application Data

[63] Continuation of Ser. No. 653,023, Sep. 21, 1984, abandoned.

[30] Foreign Application Priority Data

Nov. 1, 1983 [JP] Japan .................... 58-206225

[51] Int. Cl.$^4$ ............................................. A01N 57/10
[52] U.S. Cl. ................................................... 514/144
[58] Field of Search .......................................... 514/144

[56] References Cited

U.S. PATENT DOCUMENTS

| | | | |
|---|---|---|---|
| 2,504,404 | 4/1950 | Flenner | 514/483 |
| 2,545,948 | 3/1951 | Flenner | 514/483 |
| 4,039,635 | 8/1977 | Kato et al. | 514/131 |

OTHER PUBLICATIONS

Chemical Abstracts 98:295906; Kovacs; 1982.
"Pesticides in the Environment", vol. 2, 132–139, 144–155 (1976).

Primary Examiner—Albert T. Meyers
Assistant Examiner—John M. Kilcoyne
Attorney, Agent, or Firm—Stevens, Davis, Miller & Mosher

[57] ABSTRACT

The present invention relates to an agricultural and horticultural fungicidal composition containing as active ingredients tolclofos-methyl [O,O-dimethyl O-(2,6-dichloro-4-methylphenyl) phosphorothiaoate] and an N,N'-ethylenebis(dithiocarbamate) type fungicide.

3 Claims, No Drawings

AGRICULTURAL AND HORTICULTURAL FUNGICIDAL COMPOSITION

This application is a continuation of Ser. No. 653,023, filed Sept. 21, 1984, now abandoned.

The present invention relates to an agricultural and horticultural fungicidal composition containing as active ingredients tolclofos-methyl [O,O-dimethyl O-(2,6-dichloro-4-methylphenyl)phosphorothioate] and an N,N'-ethylenebis(dithiocarbamate) type fungicide. Tolclofosmethyl, as described in U.S. Pat. No. 4,039,635, is a compound having excellent controlling activity on soil diseases, particularly the soil disease of plants caused by pathogens belonging to genera Rhizoctonia and Corticium.

Also, it is well known that the N,N'-ethylenebis(dithiocarbamate) type fungicide, for example manganese ethylenebis(dithiocarbamate) (hereinafter referred to as maneb), zinc ethylenebis(dithiocarbamate) (hereinafter referred to as zineb), zinc.manganese ethylenebis(dithiocarbamate) complex (hereinafter referred to as manzeb) or the like, has a controlling activity on a wide range of many plant diseases, particularly the diseases of cucurbit (anthracnose, downy mildew), tomato (anthracnose, late blight), plants of crucifer group (alternaria leaf spot, white spot, downy mildew), Welsh onion (downy mildew, alternaria leaf spot, rust), strawberry (gray mold) and the like. But these N,N'-ethylenebis(dithiocarbamate) type fungicides should generally be applied in high concentrations and in high frequency, and besides their controlling activity is not always said to be satisfactory (refer to PESTICIDES IN THE ENVIRONMENT, Vol. 2, pp. 132–139, 144–155 (1976), published by Marcel Dekker, Inc.).

The present inventors, with notice given to these points, made an extensive study, and as a result, found that the present composition containing as active ingredients tolclofos-methyl and the N,N'-ethylenebis(dithiocarbamate) type fungicide has a sufficient controlling activity, in lower application concentrations than in using these compounds separately, on plant diseases such as downy mildew of grape, scab of apple, scab of pear, rust of pear, downy mildew of chinese cabbage, downy mildew of cucumber, anthracnose of cucumber, late blight of tomato, late blight of potato, cercospora leaf spot of sugar beet and the like, and therefore that the application frequency can be lowered.

When the present composition is used in controlling plant diseases, it may be used as such without adding any ingredient other than these active ingredients, but generally, it is used in the preparation-forms of wettable powder, suspension formulation, dust, etc. by mixing with solid carriers, liquid carriers, surface active agents and other auxiliaries for formulation. For the mixing ratio of tolclofos-methyl and the N,N'-ethylenebis(dithiocarbamate) type fungicide, which are an active ingredient, a range of 1:0.1 to 1:10 by weight will suffice. Also, for the content of the active ingredient in these preparations, a range of 0.1 to 99.9% by weight, preferably 0.2 to 80% by weight will suffice.

The solid carrier includes for example the fine powders or granules of kaolin clay, attapulgite clay, bentonite, terra alba, pyrophyllite, talc, diatomaceous earth, calcite, corn stalk powder, walnut shell powder, urea, ammonium sulfate, synthetic hydrated silicon dioxide and the like. The liquid carrier includes for example alcohols (e.g. isopropanol, ethylene glycol, cellosolve), water and the like.

The surface active agent used for emulsification, dispersion, wetting, etc. includes for example anionic surface active agents such as the salt of alkyl sulfate, alkyl(aryl)sulfonates, dialkyl sulfosuccinates, the salt of the phosphoric acid ester of polyoxyethylene alkylaryl ether, naphthalenesulfonic acid formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation includes for example lignosulfonates, alginates, polyvinyl alcohol, gum arabic, CMC (carboxymethyl, cellulose), PAP (isopropyl acid phosphate) and the like.

Formulation examples for the present composition will be shown. Parts in the examples are by weight.

FORMULATION EXAMPLE 1

10 Parts of tolclofos-methyl, 10 parts of maneb, 75.7 parts of kaolin clay, 4 parts of synthetic hydrated silicon dioxide and 0.3 part of PAP are thoroughly pulverized and mixed to obtain a dust.

FORMULATION EXAMPLE 2

20 Parts of tolclofos-methyl, 20 parts of manzeb, 3 parts of calcium lignosulfonate, 2 parts of sodium lauryl sulfate and 55 parts of synthetic hydrated silicon dioxide are thoroughly pulverized and mixed to obtain a wettable powder.

FORMULATION EXAMPLE 3

2.5 Parts of tolclofos-methyl, 12.5 parts of maneb, 80.7 parts of attapulgite clay, 4 parts of synthetic hydrated silicon dioxide and 0.3 part of PAP are thoroughly pulverized and mixed to obtain a dust.

FORMULATION EXAMPLE 4

5 Parts of tolclofos-methyl, 5 parts of zineb, 85.7 parts of talc, 4 parts of synthetic hydrated silicon dioxide and 0.3 part of PAP are thoroughly pulverized and mixed to obtain a dust.

FORMULATION EXAMPLE 5

2.5 Parts of tolclofos-methyl, 2.5 parts of zineb, 90.7 parts of bentonite, 4 parts of synthetic hydrated silicon dioxide and 0.3 part of PAP are thoroughly pulverized and mixed to obtain a dust.

FORMULATION EXAMPLE 6

20 Parts of tolclofos-methyl, 40 parts of maneb, 3 parts of calcium lignosulfonate, 2 parts of sodium lauryl sulfate and 35 parts of synthetic hyrated silicon dioxide are thoroughly pulverized and mixed to obtain a wettable powder.

FORMULATION EXAMPLE 7

40 Parts of tolclofos-methyl, 20 parts of zineb, 3 parts of calcium lignosulfonate, 2 parts of sodium lauryl sulfate and 35 parts of attapulgite clay are thoroughly pulverized and mixed to obtain a wettable powder.

FORMULATION EXAMPLE 8

10 Parts of tolclofos-methyl, 15 parts of manzeb, 3 parts of polyoxyethylene sorbitan monooleate, 3 parts of CMC and 69 parts of water are mixed and wet-pulverized until the particle diameter of the active ingredients is reduced to not more than 5μ to obtain a suspension formulation.

These preparations, either as such or as aqueous solutions, are scattered or sprayed onto plant bodies. The present composition may also be used in mixture with other fungicides, insecticides, acaricides, plant growth regulating agents, fertilizers and the like.

The dosage rate of the present composition is generally 0.001 to 20 kg per 10 ares, preferably 0.01 to 5 kg per 10 ares. When the preparation is used as aqueous solutions, its application concentration is 0.0005 to 5%, preferably 0.005 to 0.5%.

The controlling activity on plant diseases of the present composition will be illustrated with reference to the following test examples. Hereupon, the controlling activity is indicated by the numerical value of the control of disease (%) obtained as follows: The condition of disease of test plants on examination, i.e. the degrees of the colony and infected area on the leaves, stems, etc. of the test plants are observed with the naked eye and classified into five grades of disease index as described below, and then the disease severity (%) and control of disease (%) are calculated from the following equations.

| Disease index | Degrees of colony and infected area |
|---|---|
| 0 | No colony nor infected area is observed. |
| 0.5 | About 5% of colony or infected area is observed. |
| 1 | About 20% of colony or infected area is observed. |
| 2 | About 50% of colony or infected area is observed. |
| 4 | More than about 50% of colony or infected area is observed. |

Disease severity (%) =
$$\frac{\Sigma\{(\text{disease index}) \times (\text{number of examined leaves})\}}{(\text{number of examined leaves}) \times 4} \times 100$$

Control of disease (%) = $100 - \frac{(\text{disease severity in treated plot})}{(\text{disease severity in untreated plot})} \times 100$

TEST EXAMPLE 1

Controlling test on anthracnose of cucumber

Sandy loam was filled in a plastic pot, and cucumber (variety, Sagamihanjiro) was seeded and cultivated for 20 days in a greenhouse to obtain cucumber seedlings in the first true leaf stage. Each test compound in the preparation-form of wettable powder prepared according to Formulation example 6 was diluted with water to a prescribed concentration and sprayed onto the seedlings so that the spray liquid was thoroughly attached to the leaf surface. After spraying, the seedlings were inoculated by spraying the spore suspension of the anthracnose fungus of cucumber. After inoculation, the seedlings were cultivated at 23° C. for 2 days in a highly humid condition and then at 23° C. for further 3 days in a constant-temperature room, and the controlling activity was examined. The results are shown in Table 1.

TABLE 1

| Test compound | Dosage rate of active ingredient (ppm) | Control of disease (%) |
|---|---|---|
| Present composition | Tolclofos-methyl 50 + Maneb 100 | 90 |
| Present composition | Tolclofos-methyl 50 + Zineb 100 | 94 |
| Present composition | Tolclofos-methyl 50 + Manzeb 100 | 96 |
| Maneb | 200 | 40 |
| Zineb | 200 | 55 |
| Manzeb | 200 | 60 |

TABLE 1-continued

| Test compound | Dosage rate of active ingredient (ppm) | Control of disease (%) |
|---|---|---|
| Tolclofos-methyl | 100 | 16 |

TEST EXAMPLE 2

Controlling test on downy mildew of cucumber

Sandy loam was filled in a plastic pot, and cucumber (variety, Sagamihanjiro) was seeded and cultivated for 20 days in a greenhouse to obtain cucumber seedlings in the first true leaf stage. Each test compound in the preparation-form of wettable powder prepared according to Formulation example 7 was diluted with water to a prescribed concentration and sprayed onto the seedlings so that the spray liquid was thoroughly attached to the leaf surface. After spraying, the seedlings were inoculated by spraying the spore suspension of the downy mildew fungus of cucumber. After inoculation, the seedlings were cultivated at 20° C. for 1 day in a highly humid condition and then for further 5 days in a greenhouse, and the controlling activity was examined. The results are shown in Table 2.

TABLE 2

| Test compound | Dosage rate of active ingredient (ppm) | Control of disease (%) |
|---|---|---|
| Present composition | Tolclofos-methyl 100 + Zineb 50 | 100 |
| Present composition | Tolclofos-methyl 100 + Manzeb 50 | 100 |
| Zineb | 50 | 40 |
| Manzeb | 50 | 54 |
| Tolclofos-methyl | 100 | 10 |

TEST EXAMPLE 3

Controlling test on scab of apple

Sandy loam was filled in a plastic pot, and apple (variety, Fuji) was seeded and cultivated for 30 days in a greenhouse to obtain apple seedlings in the 4 to 5-leaf stage. Each test compound in the preparation-form of suspension formulation prepared according to Formulation example 8 was diluted with water to a prescribed concentration and sprayed onto the seedlings so that the spray liquid was thoroughly attached to the leaf surface. After spraying, the seedlings were inoculated by spraying the spore suspension of the scab fungus of apple. After inoculation, the seedlings were cultivated at 15° C. for 2 days in a highly humid condition and then for further 12 days in a constant-temperature room kept at 15° C., and the controlling activity was examined. The results are shown in Table 3.

TABLE 3

| Test compound | Dosage rate of active ingredient (ppm) | Control of disease (%) |
|---|---|---|
| Present composition | Tolclofos-methyl 200 + Maneb 200 | 100 |
| Present composition | Tolclofos-methyl 200 + Zineb 200 | 100 |
| Present composition | Tolclofos-methyl 200 + Manzeb 200 | 100 |
| Maneb | 200 | 48 |
| Zineb | 200 | 50 |
| Manzeb | 200 | 53 |
| Tolclofos- | 400 | 0 |

TABLE 3-continued

| Test compound | Dosage rate of active ingredient (ppm) | Control of disease (%) |
|---|---|---|
| methyl | | |

TEST EXAMPLE 4

Controlling test on downy mildew of grape

Sandy loam was filled in a plastic pot, and grape (variety, Neo-muscat) was seeded and cultivated for 50 days in a greenhouse to obtain grape seedlings in the 4 to 5-leaf stage. Each test compound in the preparation-form of wettable powder prepared according to Formulation example 2 was diluted with water to a prescribed concentration and sprayed onto the seedlings so that the spray liquid was thoroughly attached to the leaf surface. After spraying, the seedlings were inoculated by spraying the spore suspension of the downy mildew fungus of grape. After inoculation, the seedlings were cultivated at 23° C. for 3 days in a highly humid condition and then for further 10 days in a greenhouse, and the controlling activity was examined. The results are shown in Table 4.

TABLE 4

| Test compound | Dosage rate of active ingredient (ppm) | Control of disease (%) |
|---|---|---|
| Present composition | Tolclofos-methyl 200 + Zineb 200 | 94 |
| Present composition | Tolclofos-methyl 200 + Manzeb 200 | 96 |
| Zineb | 200 | 48 |
| Manzeb | 200 | 48 |
| Tolclofos-methyl | 400 | 11 |

TEST EXAMPLE 5

Controlling test on late blight of tomato

Sandy loam was filled in a plastic pot, and tomato (variety, Fukuju No. 2) was seeded and cultivated for 30 days in a greenhouse to obtain tomato seedlings in the 4 to 5-leaf stage. Each test compound in the preparation-form of wettable powder prepared according to Formulation example 2 was diluted with water to a prescribed concentration and sprayed onto the seedlings so that the spray liquid was thoroughly attached to the leaf surface. After spraying, the seedlings were inoculated by spraying the spore suspension of the late blight fungus of tomato. After inoculation, the seedlings were cultivated at 20° C. for 6 days in a highly humid condition, and the controlling activity was examined. The results are shown in Table 5.

TABLE 5

| Test compound | Dosage rate of active ingredient (ppm) | Control of disease (%) |
|---|---|---|
| Present composition | Tolclofos-methyl 200 + Maneb 200 | 86 |
| Present composition | Tolclofos-methyl 200 + Zineb 200 | 90 |
| Present composition | Tolclofos-methyl 200 + Manzeb 200 | 90 |
| Maneb | 200 | 42 |
| Zineb | 200 | 42 |
| Manzeb | 200 | 46 |
| Tolclofos-methyl | 400 | 14 |

What is claimed is:

1. An agricultural and horticultural fungicidal composition containing as active ingredients a fungicidally effective amount of tolclofos-methyl and a fungicidally effective amount of an N,N'-ethylenebis(dithiocarbamate) fungicide selected from the group consisting of manganese ethylenebis(dithiocarbamate), zinc ethylenebis(dithiocarbamate), and zinc-manganese ethylenebis(dithiocarbamate) complex, wherein the mixing ratio of tolclofos-methyl to the N,N'-ethylenebis(dithiocarbamate) fungicide is within a range of 10:1 to 1:10 parts by weight.

2. A preparation which comprises an an active ingredient a fungicidally effective amount of the composition according to claim 1 and at least one additive selected from the group consisting of solid carriers, liquid carriers and surface active agents for formulation.

3. A method for controlling fungi caused plant disease selected from the group consisting of diseases of downy mildew of grape, scab of apple, scab of pear, rust of pear, downy mildew of chinese cabbage, downy mildew of cucumber, anthracnose of cucumber, late blight of tomato, late blight of potato and cercospora leaf spot of sugar beet which comprises applying a fungicidally effective amount of the composition according to claim 1 to the diseased plant.

* * * * *